United States Patent [19]

Fields

[11] 4,012,454
[45] Mar. 15, 1977

[54] IODINATION PROCESS

[75] Inventor: Ellis K. Fields, River Forest, Ill.

[73] Assignee: Standard Oil Company (Indiana), Chicago, Ill.

[22] Filed: May 15, 1975

[21] Appl. No.: 577,739

[52] U.S. Cl. .................... 260/650 R; 260/283 SY; 260/290 HL; 260/327 TH; 260/329.3; 260/332; 260/332.5; 260/346.1 R; 260/346.2 R; 260/346.2 M; 260/384; 260/465 G; 260/612 D; 260/649 R

[51] Int. Cl.$^2$ .......................................... C07C 17/22

[58] Field of Search .......... 260/240, 649, 650, 576, 260/591, 607, 296, 346.2, 329.3, 283, 384

[56] References Cited

OTHER PUBLICATIONS

Haszeldine, J. Chem. Soc. (London) pp. 584–587 (1951).
Wieland et al., Ann. der Chem., vol. 446, pp. 49–77 (1926).
Bunce et al., Tetrahedron, vol. 27, pp. 5323–5335 (1971).
Bockemuller et al., Ann. der Chemie, vol. 519, pp. 165–192 (1935).
Oldham et al., J. Chem. Soc., pp. 368–375 (1941).
Ciustea et al., Chem. Abst., vol. 59; col. 6214c (1963).
Henne et al., J. Am. Chem. Soc., vol. 72, pp. 3806–3807 (1950).
Hauplschein et al., J. Am. Chem. Soc., vol. 74, pp. 849–851 (1952).
Roberts, et al., J. Am. Chem. Soc., vol. 73, pp. 5487–5488 (1951).
Demjanow et al., Berichte, vol. 40, pp. 2594–2597 (1907).
Birnbaum et al., Berichte, vol. 15, pp. 456–460 (1882).
Wilson, Organic Reactions, vol. 9, p. 358 (1957).

*Primary Examiner*—Thomas G. Todd
*Attorney, Agent, or Firm*—W. C. Clarke; Arthur G. Gilkes; William T. McClain

[57] ABSTRACT

A decarboxylation process for substituting iodine atoms for silver carboxylate radicals which comprises reacting the silver salts of carboxylic acids with iodine under decarboxylation conditions.

5 Claims, No Drawings

IODINATION PROCESS

BACKGROUND OF THE INVENTION

This invention relates to an economical one-step decarboxylation process to substitute iodine atoms for silver carboxylate radicals using silver salts of aromatic and heterocyclic carboxylic acids in a solventless procedure.

Usually a decarboxylation reaction results in the generation of carbon dioxide and the concurrent replacement with hydrogen on the molecule. For example, the decarboxylation of benzoic acid yields benzene and carbon dioxide. Pyridine carboxylic acid goes to pyridine and carbon dioxide. The presence of other carboxylic acid salts such as a sodium carboxylate of an aromatic acid will merely aid in the decarboxylation reaction and char to yield an ill-defined residue at best. However, the decarboxylation products using silver salts of carboxylic acids are silver, carbon dioxide and the coupled organic radicals of the silver carboxylates in the form of dimers, trimers, and multiples thereof. Surprisingly also, if the decarboxylation reaction takes place in the presence of iodine the decarboxylation process forms organic iodides of the reactant silver salt in a one-step process. My invention works because the use of solvents is avoided and the silver salts are heated directly with the iodine.

Among the procedures which exist for reacting halogens with the silver salts of carboxylic acids are the solvent-using Hunsdieker and Simonini reactions, as well as variations of these two reactions developed by other investigators such as Oldham and Prevost. The halogen used, the ratio of silver salt to halogen, the presence or absence of other active materials such as olefins, acetylenes or readily substituted aromatic rings and the solvent used are well-known to play a large part in determining the course of these reactions. (C. V. Wilson, *Organic Reactions*, IX, p. 332–387 (1957)) Thus, it is possible by these solvent reactions to produce organic halides containing one less carbon atom than the original acid RCOOH, (the Hunsdieker reaction); esters, RCOOR, derived from two molecules of the acid by loss of one molecule of carbon dioxide (the Simonini reaction); and halogenated aromatic compounds, XRCOOH, where X is a halogen and R is a phenyl group. These reactions can be represented by the following equations.

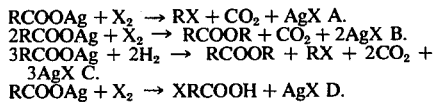

The reaction represented by A in which the molar silver salt-halogen ratio is 1:1 is the Hunsdieker reaction. The B reaction is the Simonini reaction and uses a 2:1 mole ratio of silver salt to halogen (iodine only). Reaction C is a variation of A and B by Oldham and Ubbelodhe and uses a 3:2 molar ratio. Reaction D is a variation of A and requires the presence of a phenyl group which undergoes electrophilic substitution readily.

The Hunsdieker and Simonini reactions, and the variations of these reactions developed by other investigators generally utilize non-reacting solvents. Carbon tetrachloride is considered the best general solvent for the Hunsdieker reaction. The other reactions can use benzene, carbon tetrachloride, petroleum ether, nitrobenzene or ether, as well as other solvents. The reactants are heated in a suitable solvent to cause the desired reaction.

The value of the Hunsdieker reaction in which the silver salt-halogen molar ratio is 1:1 lies in its application to aliphatic bromine compounds where it is a general preparative method. A substituent in the aliphatic chain in any position other than the α-position does not interfere with the reaction unless it is itself capable of reaction with the acyl hypohalite. In the aromatic series, the Hunsdieker reaction is not so general. Bromobenzene is formed from silver benzoate but the yields are variable and are apparently dependent upon the temperature. Although many Hunsdieker reactions involving aliphatic compounds have been described (D. I. Davies and S. J. Cristol, *Adv. In Free Radical Chem.*, *I*, 180–184 (1965); J. W. Oldham and A. R. Ubbelohde, *J. Chem. Soc.*, 368 (1941)), the Hunsdieker reaction has not been reported as giving good yields with aromatic compounds. For example, silver benzoate reacted with iodine to give only a 14% yield of iodobenzene, but no iodide was formed from silver p-nitrobenzoate. (R. A. Barnes and R. J. Prochaska, *J. Am. Chem., Soc.* 72, 3188, (1950)). The Simonini reaction has been reported categorically (C. V. Wilson, op. cit., 349) as having no value in the aromatic series. Silver benzoate gives a variety of products including the ester, the halide and halogenated benzoic acid. Silver phthalate gives phthalic anhydride.

It is, therefore, a general object of my invention to provide a new process for making aromatic and heterocyclic iodides in good yields in a convenient and economic manner using a general reaction. Another object of my invention is to provide a new process for converting silver derivatives of carboxylic acids to iodides, replacing the carboxylic acid group by a halogen. A further object of my invention is to provide a practical and economic process for the manufacture of mono and polyiodo aromatic and heterocyclic compounds directly from aromatic and heterocyclic compounds. The nature of still other objects of my invention will be apparent from a consideration of the descriptive portion to follow.

It is my discovery that the above and other objects of the invention are attained by the solventless silver salt-/iodine process herein described. I have found that aromatic and heterocyclic silver salts react with iodine without the presence of solvents to yield organic iodo and polyiodo compounds. This is quite surprising inasmuch as reactions generally go better in solvents and improved yields usually result when a suitable solvent is found.

SUMMARY OF THE INVENTION

This invention relates to a process for the production of mono and polyiodo aromatic and heterocyclic compounds which comprises the reacting of silver salts of mono and polycarboxylic acids with iodine without a solvent medium at temperatures from 100° to 270° C in mole ratios of 1–1.5 moles of iodine per atom of silver in the silver salt for 1 to 200 minutes at 1 to 100 atmospheres pressure so as to replace the carboxyl groups with iodine atoms. The silver salts have the general formula $R(COOAg)_n$ where $n$ is an integer 1 to 8 and R is an aromatic or heterocyclic ring that can contain substituents such as halogens, cyano (—CN—), nitro (—NO$_2$—), alkoxy (—OR—), alkylthiyl (—SR—), and carboxy (—COOH) radicals.

DETAILED DESCRIPTION OF THE INVENTION

Aromatic and heterocyclic mono and polyiodo compounds are prepared in a convenient manner by reacting together the silver salts of mono and polycarboxylic acids of aromatic and heterocyclic compounds and iodine in a solventless reaction at elevated temperatures. A particularly effective scheme involves adding the finely-divided silver salt to refluxing iodine.

While I do not desire to be bound by any theory concerning the reaction of this invention, it is theorized that the interaction of the reactants, the silver salt and the iodine, is caused by temperature alone and is facilitated by the absence of any external solvent. It is not required that the iodine be liquid, as the reaction does proceed at 100° C, which is below the melting point of iodine, and the iodine is in the form of a dispersed solid. Product yields of the iodo compounds are higher above 113° C, the melting point of iodine, so it may be theorized that the increased yields result from the liquid iodine being in more intimate juxtaposition with the silver salt without, in fact, solubilizing the silver salts. For purposes of this invention, the term "decarboxylation condition" is accordingly defined as consisting essentially of the application of the required reaction temperature to a silver salt in the presence of iodine.

For purposes of this invention, the terms "mono and disilver carboxylates" and "mono and disilver salts" are defined as those silver salts wherein the hydrogen of a carboxyl radical attached to an aromatic moiety, including a heterocyclic moiety, and combinations thereof, is replaced with a silver metal ion. It is also essential for purposes of this invention that the carboxylate radicals be attached directly to the aromatic or heterocyclic ring and that there be at least one silver carboxylate group per molecule.

"Aryl radical" is defined, for purposes of this invention, as a monovalent radical derived from an aromatic hydrocarbon. In terms of this invention, the term "aryl compounds" is defined as including aromatic compounds characterized by at least one benzene ring, i.e., the six carbon ring of benzene or the condensed six-carbon rings of the other aromatic derivatives such as naphthalene, phenanthrene, anthracene, etc. "Aryl carboxylic acids" are defined as aromatic compounds having at least one free valence of the aryl group attached directly to the carboxylic acid group. The term "heterocyclic compound" is defined as a compound containing a cyclic or ring structure of five or more atoms in the ring in which one or more of the atoms in the ring is an element other than carbon and can be oxygen, nitrogen and/or sulfur. The term "ring compound" is defined as an organic compound whose structure is characterized by a closed ring. It is also termed a cyclic compound. Ring or cyclic compounds can be alicyclic, aromatic (or arene) and heterocyclic. The term "iodo" refers to an iodine radical. The term "iodination" is defined as the treating or causing to combine with iodine or a compound of iodine.

My process for synthesizing aromatic and heterocyclic iodo compounds from silver carboxylates has the advantages of being a one-step process with high reaction velocity and good yields, and being applicable to aromatic and heterocyclic compounds. The Hunsdieker and Simonini, and related reactions, have the disadvantages of not being applicable to aromatic compounds and of being solvent processes with attendant complexities of using the most suitable solvent. Indeed, in the process of this invention, it is essential that a solvent be not used which also adds to the convenience of the process. The convenience of the process is demonstrated further by the fact that the reactants can be shelf items ready-for-use as needed. The utility of the novel process is well-demonstrated inasmuch as well-known compounds with known and demonstrated uses such as Rose Bengal and iodobenzene, which is used in the synthesis of compounds of positive iodine, can be made using this process.

The versatility of the novel process indeed adds to its utility. The process can be represented by the general equation:

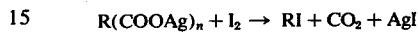

$$R(COOAg)_n + I_2 \rightarrow RI + CO_2 + AgI$$

where $n$ is an integer from one to eight and R is an aromatic or heterocyclic radical which can contain substituents such as halogens (fluorine, chlorine, bromine, (iodine), cyano (—CN), nitro (—NO$_2$), alkoxy (—OR), alkylthiyl (—SR—), and carboxy (—COOH) radicals.

Examples of the silver salts used in my invention are silver benzoate, silver 1 and 2-naphthoates, silver nicotinate, silver isonicotinate, silver thiophene-2-carboxylate, silver 2-furoate, silver p-chlorobenzoate, silver m-cyanobenzoate, silver p-nitrobenzoate, silver p-anisate, silver 2,5-dibromoterephthalate, disilver terephthalate, disilver isophthalate, trisilver trimellitate, trisilver trimesate, trisilver hemimellitate, tetrasilver pyromellitate, tetrasilver mellophenate, pentasilver benzenepentacarboxylate, hexasilver mellitate, disilver salts of naphthalene 1,3-; 1,4-; 1,5-; 1,6-; 1,7-; 1,8; 2,4-; 2,6-; and 2,7-dicarboxylic acids, tetrasilver 1,4,5,8-naphthalenetetracarboxylate, octasilver naphthaleneoctacarboxylate, disilver pyridine 2,4-; 2,5-; 2,6-; 3,5-; and 3,6- dicarboxylates, disilver thiophene-2,5-dicarboxylate, and the silver salts of di-, tri-, and tetracarboxylic acids of anthracene, anthraquinone, phenanthrene, chyrsene, perylene, quinoline, isoquinoline, phenanthridine, benzothiophene, (thianaphthene), dibenzothiophene, benzofuran, and dibenzofuran.

Included in the silver salts used in my invention are those of the general formula

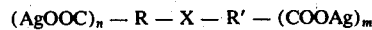

$$(AgOOC)_n - R - X - R' - (COOAg)_m$$

where R and R' are the same or different aryl or heterocyclic radicals, $n$ and $m$ are integers of 1 to 4, and X is a divalent atom or radical such as —O—, —S—, —NH—, —CH$_2$—,

—SO$_2$—, —CH=CH—, or —C ≡ C—. Examples of these silver salts are disilver diphenylether-4,4'-dicarboxylate, disilver methylene-3,3'-dibenzoate, disilver diphenylsulfone-4,4'-dicarboxylate, disilver benzophenone-4,4'-dicarboxylate, tetrasilver benzophenone-3,3',4,4'-tetracarboxylate, disilver stilbene-4,4'-dicarboxylate, and disilver diphenylacetylene-4,4'-dicarboxylate.

It is understood that the above equation is not quantitative but merely represents qualitatively the general aspects of the novel process.

If it is desired to iodinate aromatic compounds and heterocyclic compounds of aromatic nature, the decarboxylation reaction is run by heating the silver salts and iodine together in mole ratios of 1–1.5 moles of iodine per atom of silver in the silver salt, at 100° C to 270° C for 1 to 200 minutes. Preferred conditions are 140° to 190° C for five to ten minutes. The reaction can be conducted at one to 100 atmospheres pressure. A particularly effective technique involves adding the finely-divided silver salt to refluxing iodine.

In order to facilitate a clear understanding of the invention, i.e., the novel decarboxylation process to substitute iodine atoms for silver carboxylate radicals, the following specific embodiments are described in detail. It should be understood, however, that the detailed expositions of the application of the invention, while indicating preferred embodiments, are given by way of illustration only since various changes and modifications within the spirit and scope of the invention will become apparent to those skilled in the art from this detailed description.

EXAMPLE I 4.58 Grams (0.02 mole) of silver benzoate and 10.16 grams (0.04 mole) of iodine were mixed intimately in a Waring blender with Teflon coated blades, then heated in a round-bottomed flask at 140°–180° C for 10 minutes. The mixture was allowed to cool to room temperature. The cooled mixture was then extracted with two 100 ml. portions of ether. The composited ether solution was decolorized by stirring with 100 ml of 5(wgt)% aqueous sodium bisulfite, dried over anhydrous calcium sulfate, filtered and evaporated. The 3.4 gram residue was 56.4% iodobenzene, 3.0% iodobiphenyl and 1.9% diiodobiphenyl. The remainder was not identified. Analysis was by gas chromatography.

EXAMPLE II

In a similar procedure as in Example I, 7.6 grams (0.02 mole) of disilver isophthalate and 10.16 grams (0.04 mole) of iodine were intimately mixed and heated to 140° C. A vigorous reaction occurred and the temperature rose to 170° C. The cooled mixture was extracted with three 100 ml. portions of ether, decolorized with successive portions of 100 ml. of 5(wgt)% sodium bisulfite, dried, filtered and evaporated. The 2.4 gram residue analyzed 61% 1,3-diiodobenzene, 0.0049% iodobiphenyl, 1.15% diiodobiphenyl, 2.95% triiodobiphenyl, and 0.0033% tetraiodobiphenyl.

EXAMPLE III 7.6 Grams (0.02 mole) of disilver terephthalate and 10.15 grams (0.04 mole) of iodine were intimately mixed and heated to 145° C. The temperature rose to 175° C where it was kept for 10 minutes. The cooled mixture was extracted with three 100 ml portions of ether which was then dried, filtered and evaporated. The 2.65 gram residue contained 2.3 grams of 88% pure p-diiodobenzene, m.p. 126°–127° C. The residue also contained 1.14% iodobiphenyl, 1.13% diiodobiphenyl, and 3.41% triiodobiphenyl. Analysis was by gas chromatography and mass spectroscopy.

EXAMPLE IV 7.6 Grams (0.02 mole) of disilver phthalate and 10.16 grams (0.04 mole) of iodine were heated at 150°–160° C for 10 minutes. After the mixture was cooled, two 100 ml. ether extractions yielded 1.8 grams of o-diiodobenzene, 96% pure, m.p. 24°–26° C. The 1.8 gram residue also contained 0.0052% triiodobiphenyl. Analysis was by gas chromatography and mass spectroscopy.

EXAMPLE V 5.31 Grams (0.01 mole) of trisilver trimesate and 7.62 grams (0.03 mole) of iodine, intimately mixed, were heated to 160° C for 10 minutes. Ether extractions, two 100 ml. each, yielded a 3.3 gram residue, 66% of which was 1,3,5-triiodobenzene. Analysis was by gas chromatography.

EXAMPLE VI 5.4 Grams (0.01 mole) of finely-powdered disilver 2.5-dibromoterephthalate was added to 5.6 grams (0.022 mole) of iodine at reflux in a round bottom flask. Heating at 185° C continued for 10 minutes. The cooled mixture was extracted with ether. The ether solution was washed with 100 ml. of 10% aqueous sodium thiosulfate, then 50 ml. of 5% aqueous sodium hydroxide, dried, filtered and evaporated. The 1.4 gram residue contained 47.8% 1,4-diiodo-2,5-dibromobenzene. No evidence was found of coupled products. Analysis was by gas chromatography and mass spectroscopy.

EXAMPLE VII 5.6 Grams (0.02 mole) of powdered silver 1-naphthoate was added to 5.6 grams (0.02 mole) of refluxing iodine in a round-bottom flask. The refluxing was continued for five minutes, approximately 180°–185° C. The mix was cooled and extracted with two 100 ml. portions of ether. The filtered ether solution was evaporated to obtain a 1.9 gram residue, 67.1% of which was 1-iodonaphthalene. Analysis was by gas chromatography.

EXAMPLE VIII 4.6 Grams (0.02 mole) of powdered silver nicotinate was added to 5.6 grams (0.02 mole) of refluxing iodine in a round bottom flask. The mixture was kept at 180°–185° C for five minutes, then cooled and extracted with two 100 ml portions of ether. The filtered ether solution on evaporation yielded 1.4 grams of residue which was 36.8% 3-iodopyridine, 3.4% bipyridyl and 0.4% iodopyridyl. Analysis was by gas chromatography and mass spectroscopy.

EXAMPLE IX 2.74 Grams (0.01 mole) of silver 4-nitrobenzoate and 5.08 grams (0.02 mole) of iodine were milled together to form an intimate mixture. The mixture was heated rapidly in a combustion tube under nitrogen to 200° C and kept at that temperature for one minute. The cooled mixture was extracted with 200 ml. of ether. The ether solution was washed successively with 50 ml. of 10% aqueous sodium thiosulfate to remove excess iodine and two 50 ml. portions of water. The solution was then dried over anhydrous calcium sulfate and filtered. The ether was evaporated off on a steam bath. The residue, 3.0 grams, analyzed 50% 4-iodonitrobenzene by gas chromatography, a yield of 60.2 mole %.

What is claimed is:

1. A decarboxylation iodination process for substituting iodine atoms for silver carboxylate radicals which comprises reacting a composition consisting essentially of iodine and the silver salt of a carboxylic acid at a temperature of about 100° to 270° C in mole ratios of about 1.0 to 1.5 moles of iodine per mole equivalent of silver in said silver salt at a pressure from 1 to 100 atmospheres, wherein finely-divided said silver salt is added to said iodine under refluxing conditions, the said carboxylic acid being selected from the group of carboxylic acids consisting of isophthalic acid, 2,5-dibromoterephthalic acid, terephthalic acid and trimesic acid.

2. A decarboxylation iodination process for substituting iodine atoms for silver carboxylate radicals which comprises reacting a composition consisting essentially of iodine and the silver salt of a carboxylic acid at a temperature of about 100° to 270° C in mole ratios of about 1.0 to 1.5 moles of iodine per mole equivalents of silver in said silver salt at a pressure from 1 to 100 atmospheres, said silver salt being a disilver salt of isophthalic acid.

3. A decarboxylation iodination process for substituting iodine atoms for silver carboxylate radicals which comprises reacting a composition consisting essentially of iodine and the silver salt of a carboxylic acid at a temperature of about 100° to 270° C in mole ratios of about 1.0 to 1.5 moles of iodine per mole equivalents of silver in said silver salt at a pressure from 1 to 100 atmospheres, said silver salt being a disilver salt of 2,5-dibromoterephthalic acid.

4. A decarboxylation iodination process for substituting iodine atoms for silver carboxylate radicals which comprises reacting a composition consisting essentially of iodine and the silver salt of a carboxylic acid at a temperature of about 100° to 270° C in mole ratios of about 1.0 to 1.5 moles of iodine per mole equivalents of silver in said silver salt at a pressure from 1 to 100 atmospheres, said silver salt being a disilver salt of terephthalic acid.

5. A decarboxylation iodination process for substituting iodine atoms for silver carboxylate radicals which comprises reacting a composition consisting essentially of iodine and the silver salt of a carboxylic acid at a temperature of about 100° to 270° C in mole ratios of about 1.0 to 1.5 moles of iodine per mole equivalents of silver in said silver salt at a pressure from 1 to 100 atmospheres, said silver salt being a trisilver salt of trimesic acid.

* * * * *

UNITED STATES PATENT OFFICE
CERTIFICATE OF CORRECTION

Patent No. 4,012,454          Dated March 15, 1977

Inventor(s) Ellis K. Fields

It is certified that error appears in the above-identified patent and that said Letters Patent are hereby corrected as shown below:

Column 1, line 50, "RCOOAg + $X_2 \longrightarrow$ RX + $CO_2$ + AgX A." should read -- A) RCOOAg + $X_2 \longrightarrow$ RX + $CO_2$ + AgX --.

Column 1, line 51, "2RCOOAg + $X_2 \longrightarrow$ RCOOR + $CO_2$ + 2AgX B." should read -- B) 2RCOOAg + $X_2 \longrightarrow$ RCOOR + $CO_2$ + 2AgX --.

Column 1, line 52, "3RCOOAg + $2H_2 \longrightarrow$ RCOOR + RX + $2CO_2$ + 3AgX C." should read -- C) 3RCOOAg + $2X_2 \longrightarrow$ RCOOR + RX + $2CO_2$ + 3AgX --.

Column 1, line 54, "RCOOAg + $X_2 \longrightarrow$ XRCOOH + AgX D." should read -- D) RCOOAg + $X_2 \longrightarrow$ XRCOOH + AgX --.

Signed and Sealed this twenty-sixth Day of July 1977

[SEAL]

Attest:

RUTH C. MASON
*Attesting Officer*

C. MARSHALL DANN
*Commissioner of Patents and Trademarks*